US008892183B2

(12) United States Patent
Gericke et al.

(10) Patent No.: US 8,892,183 B2
(45) Date of Patent: Nov. 18, 2014

(54) METHOD FOR PLANNING A COMBINED EXAMINATION OF AN EXAMINATION OBJECT

(75) Inventors: Ralph Gericke, Gerhardshofen (DE); Annette Gumbrecht, Herzogenaurach (DE); Dorothea Laux, Erlangen (DE); Diana Martin, Herzogenaurach (DE); Mike Müller, Möhrendorf (DE); Carsten Prinz, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 794 days.

(21) Appl. No.: 12/318,999

(22) Filed: Jan. 14, 2009

(65) Prior Publication Data
US 2009/0182219 A1 Jul. 16, 2009

(30) Foreign Application Priority Data
Jan. 15, 2008 (DE) .......................... 10 2008 004 469

(51) Int. Cl.
*A61B 5/05* (2006.01)
*A61B 6/03* (2006.01)
*A61B 6/00* (2006.01)
*A61B 19/00* (2006.01)
*A61B 5/055* (2006.01)

(52) U.S. Cl.
CPC ............... *A61B 6/037* (2013.01); *A61B 6/5247* (2013.01); *A61B 19/52* (2013.01); *A61B 5/055* (2013.01); *A61B 2019/5289* (2013.01)
USPC ....................................................... 600/407

(58) Field of Classification Search
CPC ...... A61B 6/037; A61B 6/5247; A61B 5/055; A61B 19/52; A61B 2019/5289
USPC ....................................................... 600/407
See application file for complete search history.

(56) References Cited

U.S. PATENT DOCUMENTS

2005/0206967 A1   9/2005  Viswanth et al.
2008/0135769 A1*  6/2008  Rosen ...................... 250/363.09

FOREIGN PATENT DOCUMENTS

| DE | 10154740      | 6/2002  |
| DE | 10319085      | 11/2004 |
| DE | 102005031901  | 1/2007  |
| DE | 102005031902  | 1/2007  |
| DE | 102006010535  | 9/2007  |
| DE | 102007009183  | 8/2008  |
| WO | WO 2007/061775 | 5/2007 |

OTHER PUBLICATIONS

Gaa et al., Whole-Body Imaging With PET/MRI, Eur J Med Res, 9: 309-312, 2004.*

* cited by examiner

*Primary Examiner* — Long V. Le
*Assistant Examiner* — Bo J Peng
(74) *Attorney, Agent, or Firm* — Harness, Dickey & Pierce, P.L.C.

(57) ABSTRACT

A method for planning a combined examination of an examination object using two imaging modalities is disclosed, with measurements being taken in at least two regions of the examination object. In at least one embodiment, the method includes planning of at least one measuring protocol of the first modality, which includes at least one measurement in a first of the regions and at least one measurement in a second of the regions; planning of at least one measuring protocol of the second modality, which comprises at least one measurement in the first region; and automatic production of a combined measuring sequence by arranging the measurements in such a manner that carrying out the measuring sequence taking into account modality preparations to be carried out between measurements takes as little time as possible.

In at least one embodiment, the automated production of the actual measuring sequence allows the measuring protocols of the individual modalities to be planned in a simple manner for a number of regions. The focus can therefore be on diagnostic questions at the measurement planning stage.

20 Claims, 2 Drawing Sheets

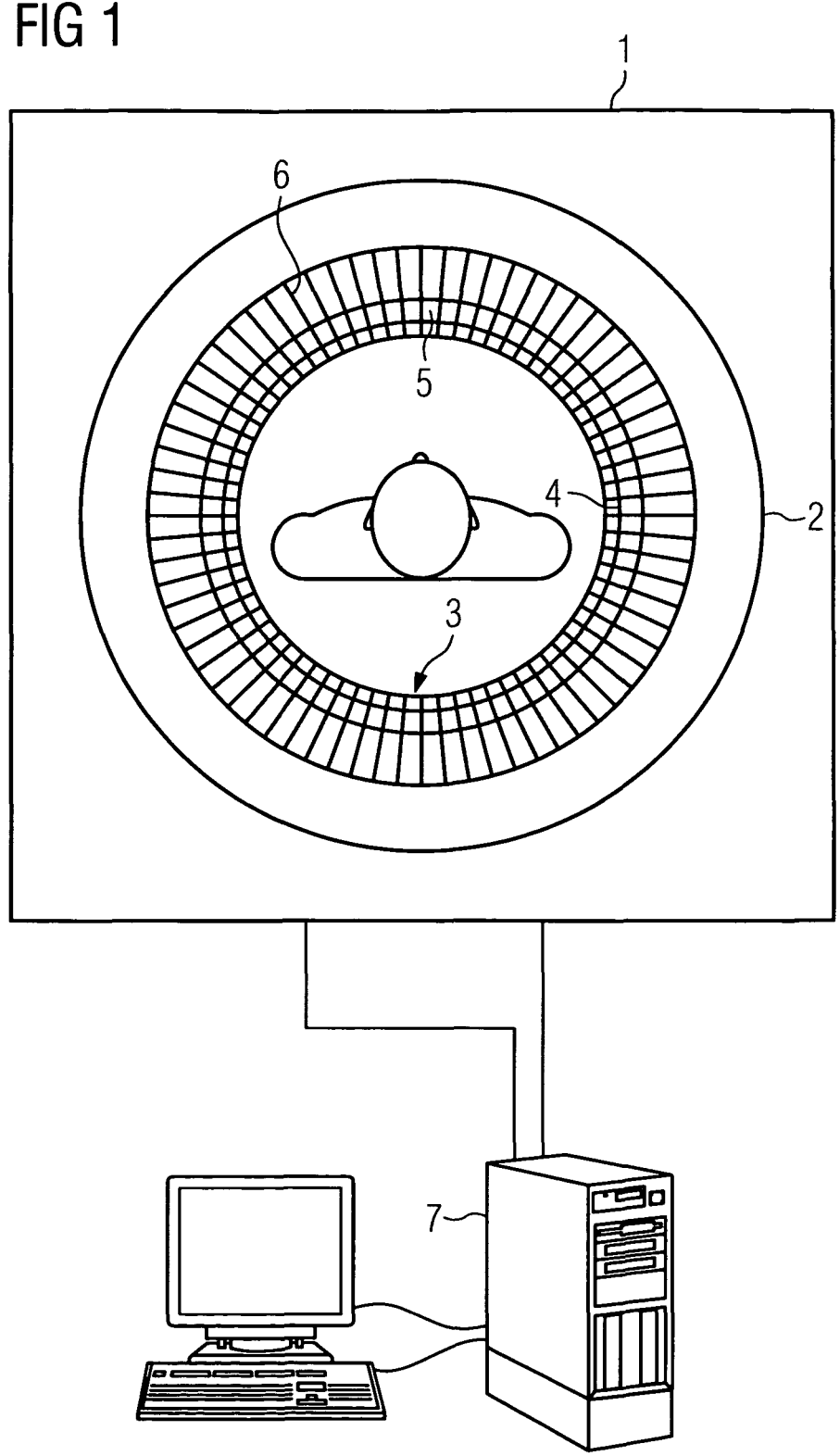

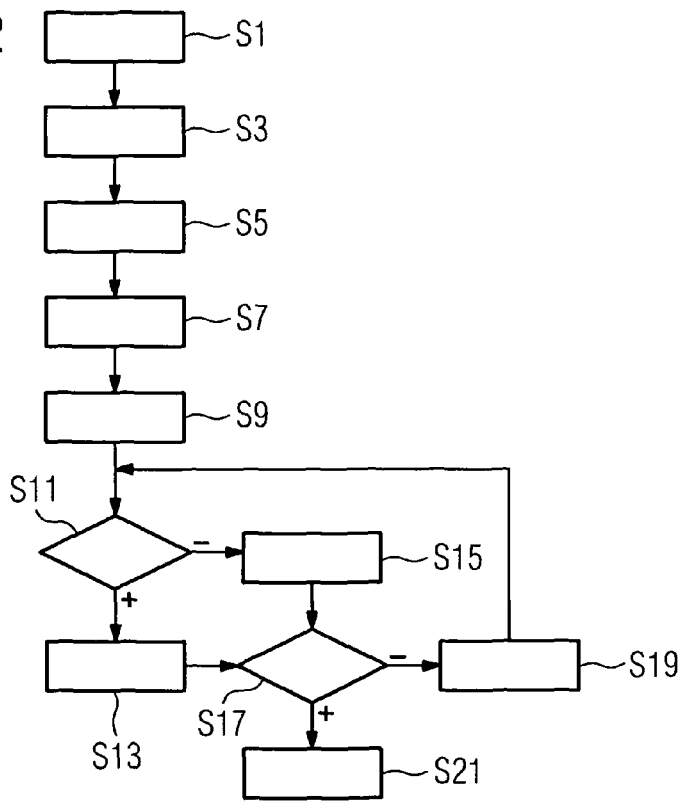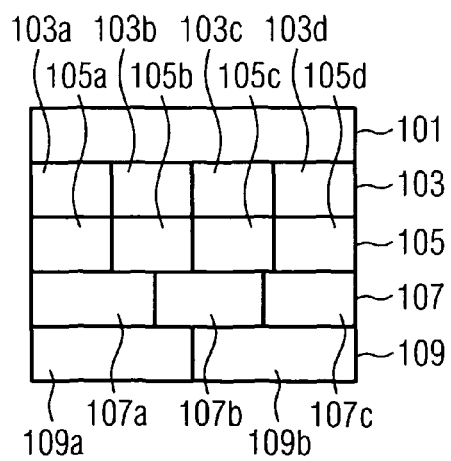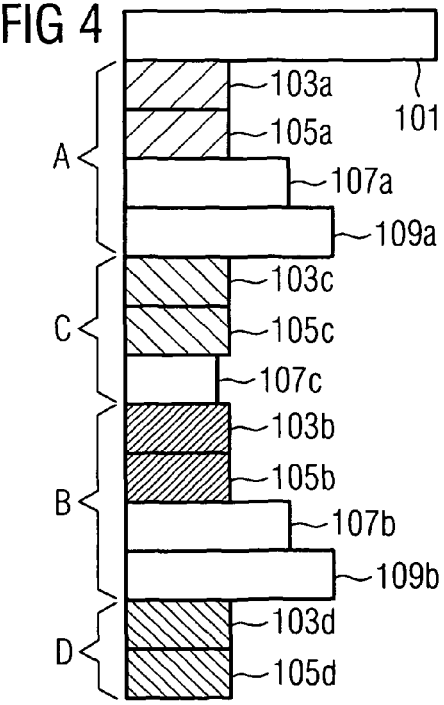

METHOD FOR PLANNING A COMBINED EXAMINATION OF AN EXAMINATION OBJECT

PRIORITY STATEMENT

The present application hereby claims priority under 35 U.S.C. §119 on German patent application number DE 10 2008 004 469.5 filed Jan. 15, 2008, the entire contents of which is hereby incorporated herein by reference.

FIELD

Embodiments of the present invention generally relate to a method for carrying out a combined examination using two imaging modalities and/or a method for carrying out a combined examination.

BACKGROUND

So-called "hybrid modalities", such as PET-CT, SPECT-CT, PET-MR and SPECT-MR for example, have become increasingly important in medical imaging in recent times. These refer to the following:
PET: Positron Emission Tomography
CT: Computed Tomography
SPECT: Single Photon Emission Computed Tomography
MR: Magnetic Resonance Tomography The advantage of such combinations is the connection of one modality with high local resolution (in particular MR or CT) to a modality with high sensitivity (in particular SPECT or PET). Reference is made below to a combined PET-MR system. Embodiments of the present invention can however generally be used for all forms of hybrid modalities or associated measuring methods.

An MR system generally includes a control computer, a measuring system and an image computer. A measuring program runs on the control computer, activating the measuring system to record MR images according to the planned measuring sequence. A measuring program here generally includes a number of program steps and optionally measuring breaks, during which operators can for example adjust the patient support or administer contrast agent to a patient. Each program step is assigned a measuring protocol, which controls the physical parameters of the measuring system for measuring purposes.

PET uses the particular characteristics of the positron emitter and positron annihilation to determine the functions of organs or cell regions quantitatively. For this corresponding radiopharmaceuticals marked with radionuclides are administered to the patient before the examination. As they decay the radionuclides emit positrons, which after a short distance interact with an electron, with the result that so-called annihilation occurs. This produces two gamma quanta, which fly apart in opposing directions (with a 180° offset). The gamma quanta are captured by two opposing PET detector modules within a specific time window (coincidence measurement), with the result that the annihilation site is determined at a position on the connecting line between these two detector modules.

To show this the PET detector module must generally cover a large part of the gantry arm length. It is divided into detector elements with side lengths of a few millimeters. During detection of a gamma quantum each detector element generates an event record, indicating the time and evidence site, i.e. the corresponding detector element. This information is transmitted to a high-speed logic unit and compared there. If two events coincide at a temporal maximum interval, a gamma decay process on the connecting line between the two associated detector elements is assumed. The PET image is reconstructed using a tomography algorithm, i.e. so-called back projection.

The different requirements for the modalities combined in a hybrid modality in respect of measurement planning means that the planning of an optimum measuring sequence is a demanding task for operators. For optimum diagnostic evaluation of data records acquired using hybrid modalities it is essential to prepare for and carry out the examination in an appropriate manner.

Established methods use sequential recording by both modalities. This means that a sequential order results even during acquisition planning. CT measurements and PET measurements are thus planned one after the other.

For simultaneous acquisition by two modalities, as is possible for example with the PET-MR hybrid modality, it is however desirable to have an option which both enhances user-friendliness and also optimizes the quality of the result data.

MR examinations deploy techniques, with which a fairly large region of the body can be examined, in that the patient couch with the patient supported thereon is passed through the magnet, with examinations being carried out in different couch positions. This makes it possible to examine regions of the body which are larger than the examination volume available to the system.

A body region is examined here, which is larger than the available image field, in that a number of so-called levels are measured. The body region is broken down into individual segments and a measurement, which may for example contain a number of sub-measurements, is taken for each segment in an associated couch position. By examining different body regions it is possible for example to record the body as a whole, with this being done at different levels (couch positions or imaging regions). The images recorded at each level each have measuring parameters such as echo time, repetition time, layer thickness, number of layers, voxel size, layer orientation, etc. for example.

SUMMARY

In at least one embodiment of the present invention a method is specified for planning a combined examination, which allows simultaneous acquisition by two modalities without adversely affecting user-friendliness and the quality of result data.

The method for planning a combined examination of an examination object using two imaging modalities, in at least one embodiment, allows measurements to be taken in at least two regions of the examination object and comprises:
planning of at least one measuring protocol of the first modality, which comprises at least one measurement in a first of the regions and at least one measurement in a second of the regions,
planning of at least one measuring protocol of the second modality, which comprises at least one measurement in the first region and
automatic production of a combined measuring sequence by arranging the measurements (103a-109b) in such a manner that carrying out the measuring sequence taking into account modality preparations to be carried out between measurements (103a-109b) takes as little time as possible.

Automated production of the combined measuring sequence allows the measuring protocols of the respective modalities to be planned individually. Compared with the alternative option of planning the combined measuring sequence manually in one pass and thereby planning the individual measurements of the different modalities individually in a temporally expedient sequence, the complete planning of the measuring protocols of the first and second modalities independently of one another represents a significant simplification. Operators of the modalities therefore do not have to worry about the temporal arrangement of the individual measurements in the measuring sequence. Therefore the focus can be on diagnostic questions at the planning stage. In particular it is an advantage of the automatic production of the combined measuring sequence that measurements that can be executed in parallel on both modalities are executed at identical times in the measuring sequence. This allows time to be saved during subsequent implementation of the measuring sequence.

In one advantageous embodiment of the invention when arranging the measurements those measurements with identical examination regions are grouped into groups and the groups are arranged one after the other in the sequence. This saves time when executing the measuring sequence, as it minimizes modality preparations (e.g. moving the patient couch). Preparations for measurements in a different region in particular require greater preparation time outlay.

In one advantageous embodiment of the invention the measurements are arranged in such a manner that measurements that can be executed in parallel by both modalities are executed at identical times in the measuring sequence. This also saves time when implementing the measuring sequence as any measurements that can be executed in parallel are automatically executed simultaneously.

In one advantageous embodiment of the method the production of the combined measuring sequence comprises:
  the measuring protocols of the modalities are broken down into individual measurements,
  the regions to be examined for the measurements are compared,
  measurements that can be executed in parallel by the two modalities are identified and
  measurements that can be executed in parallel are accordingly arranged simultaneously in the measuring sequence.

By breaking down the collectively planned measuring protocols of the modalities into individual measurements and comparing the region to be examined in each instance it is possible to identify measurements that can be executed in parallel. These are then arranged accordingly in the measuring sequence. This offers an efficient method for executing measurements that can be executed in parallel simultaneously in the measuring sequence, thereby saving measuring time.

In a further advantageous embodiment of the method the identification of measurements that can be executed in parallel comprises:
  determining the relative position of the examination volumes of the two modalities,
  determining measurements of different modalities, for which the relative position of the regions to be examined is identical to the determined relative position of the examination volumes.

This embodiment of the identification of the measurements to be executed in parallel takes account of the different structures of hybrid modalities. It is thus possible on the one hand for the examination volumes of the two modalities not to be arranged isocentrically. This is the case for example with known PET-CT devices. Here measurements can be executed simultaneously, for which the relative position of the regions to be examined corresponds to the relative position of the examination volumes. In this instance a PET examination and a CT examination can be executed simultaneously. In another instance, e.g. with PET-MR devices, the examination volumes of the PET and MR components of the hybrid modality have isocentric examination volumes. However the sizes of the examination volumes can be different. In this instance measurements of the same body region can be taken in parallel, which is preferable for time-saving reasons.

In one advantageous method, in at least one embodiment in which the modalities are present in a combined diagnosis apparatus and the regions of the examination object to be examined can be brought into the examination volume by moving a patient couch, the combined measuring sequence is produced in such a manner that the number of movements of the patient couch during the measuring sequence is minimized. Such an execution of the method enhances the patient's comfort and reduces measuring time, as the number of movements of the patient couch is kept as low as possible.

If none of the measurements to be taken can be executed in parallel, in an alternative embodiment of the invention a minimum number of movements of the patient couch can be used as a basis solely when producing the combined measuring sequence. In this instance the measurements are arranged in such a manner that the number of movements of the patient couch is minimized.

BRIEF DESCRIPTION OF THE DRAWINGS

Further advantages and embodiments of the invention will emerge from the example embodiments described below in conjunction with the figures, in which:

FIG. 1 shows a schematic diagram of a PET-MR combination device,

FIG. 2 shows a schematic flow diagram of an embodiment of the invention,

FIG. 3 shows a schematic diagram of a planned measurement and

FIG. 4 shows a schematic diagram of a measuring sequence.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The example embodiments of the invention can be used, for example, for a combined PET-MR device. A combined device has the advantage that both MR and PET data can be obtained isocentrically. This allows the examination volume within the region of interest to be defined precisely using the data of the first modality (PET) and this information to be used in the further modality (e.g. magnetic resonance). Transmission of the volume information relating to the region of interest from an external PET device to an MR device is possible but registration of the data requires greater outlay. Generally all the data that can be defined using magnetic resonance or other imaging methods can be determined from the region of interest selected in the PET data record. For example fMRI data, diffusion data, T1 or T2 weighted images or quantitative parameters can be obtained in the region of interest by way of magnetic resonance examinations instead of spectroscopy data. Similarly computed tomography methods (e.g. perfusion measurement, multiple energy imaging) or x-ray can be deployed.

It is however also additionally possible to display different biological characteristics in the PET data record using a number of so-called tracers, thereby further optimizing the region of interest and the volume determined through this or to select a number of different examination volumes in one go, which are then analyzed in subsequent examinations.

Similarly the example embodiments of the invention can also be applied to hybrid modalities with non-isocentric examination volumes, such as known PET-CT systems for example.

FIG. 1 shows a known apparatus 1 for overlaid MR and PET image displays. The apparatus 1 includes a known MR tube 2. The MR tube 2 defines a longitudinal direction z, which extends orthogonally in relation to the plane of the drawing in FIG. 1.

As shown in FIG. 1, a number of PET detection units 3, which are arranged opposite each other in pairs around the longitudinal direction z, are arranged coaxially within the MRI tube 2. The PET detection units 3 include, for example, an APD photodiode array 5 with an upstream array of LSO crystals 4 and an electric amplifier circuit (AMP) 6. Embodiments of the invention are however not restricted to the PET detection units 3 with the APD photodiode array 5 and the upstream array of LSO crystals 4 but other types of photodiodes, crystals and apparatuses can equally be used for detection.

Image processing to produce the overlaid MR and PET image display is carried out by a computer 7.

The MR tube 2 defines a cylindrical first image field along its longitudinal direction z. The plurality of PET detection units 3 defines a cylindrical second image field along the longitudinal direction z. According to an embodiment of the invention the second image field of the PET detection units 3 essentially corresponds to the first image field of the MR tube 2. This is realized by corresponding adjustment of the arrangement density of the PET detection units 3 along the longitudinal direction z.

To plan examinations an overview recording of an object is preferably generally first produced with low resolution using the MR method. Such overview recordings are also referred to as scouts.

The planning for the actual MR and PET measurements is now carried out based on the overview recording. The planning for the MR and PET measurements is generally based on the already produced overview recording in each instance.

The planning includes for example the generally known setting of the parameters required for the MR and PET measurements, such as for example the image fields FoV (field of view), the layer thicknesses and the layer intervals, the measurement volume, the weightings of the MR sequences (T1, T2), etc.

To implement the simultaneous planning of the MR and PET measurements a suitable user interface is provided by way of the computer 7, to define a common coordinate system for the MR and PET measurements. The measurements are planned in the user interface of the system.

The MR and PET measurements can also be planned on images of the linked modalities, for example not only based on MR data but also based on PET data or merged data. This requires a further overview recording produced using the MR method.

After planning, the planned MR and PET measurements are taken. The measuring sequence used for this is produced from the planned measuring protocols of the individual modalities by means of a method according to the example embodiment of the present invention.

The measuring fields (FoV) of the measurements taken simultaneously are displayed simultaneously on the same planning images in each instance and can be modified/adjusted together or separately, graphically for example. The visualization can be switched with user control, for example to display just the MR measurement, just the PET measurement or a combined display. The PET reconstruction volume can also be adjusted graphically in a direct manner, for example to the MR examination volume.

For examinations, which run over a larger measuring region, for example whole body recordings, all the levels or the complete examination volume, even subdivided into a number of measuring steps, can be visualized. This allows the respective measuring protocol of the modality to be planned in a simple manner.

During measuring and/or image reconstruction by the one or both modalities, the user can advantageously carry out further planning. As soon as reconstructed data of at least one of the two modalities is available, this data can be used to plan subsequent measuring processes. The progress of the respective measuring processes (or reconstructions) is constantly visualized for the user.

This advantageously increases both ease of operation for the user and the quality of the result data, as the measurements of both modalities can be mapped perfectly onto one another.

FIG. 2 shows a schematic flow diagram of an example embodiment of the invention. In a method step S1 an operator plans a measuring protocol of the first modality in one step. This measuring protocol can include a number of measurements in different body regions (levels) of the patient. In a subsequent step S3 a measuring protocol of the second modality is planned by the operator. This takes place in one step again and can include different measurements taken at different body regions of the patient. Unified planning for example has the advantage that, once they have been set, the measuring parameters of one level can be adopted in a simple manner for the other levels of the modality without operators having to take any action.

In a method step S5 the planned measuring protocols are broken down into individual measurements, so that these can then be rearranged in a combined measuring sequence. In a fourth method step S7 one of the measurements is selected. In a fifth method step S9 a second measurement is selected, which is compared in method step S11 with the measurement selected in method step S7. The comparison determines whether the two measurements can be executed simultaneously in respect of their examination regions and the examination volumes of the two modalities. If so, in a method step S13 the first and second measurements are marked as being able to be executed in parallel. If not, in a method step S15 the first measurement is marked as not being able to be executed in parallel with the second measurement. In a method step S17 it is checked whether all the measurements have been compared in pairs. If not, in a method step S19 a pair of measurements that has not yet been compared is selected. The method then continues with method step S11. If in method step S11 all the measurements have been compared in pairs, in a method step S21 a measuring sequence is produced, in which the measurements marked in method step S13 are executed simultaneously in each instance.

The described example embodiments describe the situation for application to hybrid modalities with two combined modalities. In principle the example embodiments can be extended to any number of combined modalities. Similarly it is not necessary for the acquisitions of the two modalities to take place isocentrically. It is possible for the modalities to be ranged one behind the other, as is known for example with PET-CT devices and for the acquisition of different regions to take place in a synchronized manner.

In the instance described and in the case of an isocentrically structured PET-MR device the individual measuring steps are not necessarily of the same duration. Thus for example a number of PET acquisitions can be carried out during a single MR acquisition and vice versa. When producing the combined measuring sequences it is ensured that the highest possible number of acquisitions of the different modalities are processed in a parallel manner, to save time.

FIG. 3 shows a schematic diagram of an example of a sequence of measuring protocols. It comprises a number of measuring protocols 101 to 109, which use different modalities. Thus for example the measuring protocol 101 is a scout, in which important measuring parameters are determined for subsequent measurements. Only the PET modality uses the measuring protocol 103. The measuring protocols 105 to 109 are different MR examinations, which are to be carried out on the patient. Different diagnostic questions can be dealt with in this process. Thus for example the measuring protocol 105 can provide an overview image and attenuation values for correction of the PET data. Contrast agent is used in the measuring protocol 107, while a "Short Inversion Recovery" sequence is deployed in the measuring protocol 109. Each of the measuring protocols 101 to 109 can comprise different examination regions, in which the measuring parameters are set identically in each instance. Thus for example in the measuring protocol 103 the entire upper body of the patient can be examined in a number of steps. The same applies to the measuring protocols 105 to 109.

The measuring protocol 103 therefore includes four measurements 103a to 103d, each measuring different regions of the patient using identical measuring parameters. Generally the number of measurements within a measuring protocol is not restricted. The measuring protocol 105 includes measurements 105a to 105d, while the measuring protocol 107 only includes measurements 107a to 107c. The measuring protocol 109 comprises two measurements 109a and 109b.

When planning complete measuring protocols the same parameters are used for a number of regions of the patient, without operators having to remember the parameters of the previously used measuring protocol or having to recapture these. Within the measuring protocol 103 provision can be made for an MR acquisition in addition to the PET acquisition, in order to determine the attenuation correction factors required to correct the PET signal. It is possible for the same body regions of the patient to be examined with the respective measurements in each of the measuring protocols 101 to 109. However this is not essential. Thus it is also possible for a whole or partial body examination to be carried out using the PET measurement in the measuring protocol 103 and this is similarly the case in the measuring protocol 105. However in the measuring protocols 107 and 109 only selected regions, for example of the upper body or legs, can be examined. Such planning allows different measuring protocols to be planned in an individual and flexible manner for different regions of the patient. The described method sequence allows a measuring protocol, which is to be executed over a number of regions, to be planned in a single working step. The measuring parameters of the measuring protocol are thus largely identical in all the measurements. The exceptions are parameters, which are specific to a body region, for example the position of the patient table.

In a further example embodiment of the invention provision is made for a default to be set in respect of the regions of the patient to be measured within one of the planned measuring protocols, for example the PET measuring protocol 103. When producing the combined measuring sequences it is taken into account that the position of the patient couch in the measuring sequence is only changed, when all the measurements of the one modality have been taken in the current couch position. However couch movement is delayed until the second modality has completed its measurements, which also impacts on the start of measuring the next region.

FIG. 4 shows a schematic diagram of a measuring sequence, generated from the measuring protocols in FIG. 3 with a example embodiment of the present invention. The order of the individual measurements in the measuring protocols 101 to 109 was rearranged by the method and optimized in respect of the position of the patient couch and maximum parallelism of execution of the measurements. The measuring sequence starts with the measuring protocol 101, which is at the beginning. In a subsequent part A of the measuring sequence all the measurements that can be taken with the patient couch in a specific position, for example at the head, are combined. Individually these are the measurements 103a to 109a. The measurements 103a (PET measurement) and 105a (MR measurement) can be executed in parallel and are therefore shown hatched in FIG. 4. They are executed in parallel when the measuring sequence is carried out. Because the MR modality is busy with the measurement 105a the measurements 107a and 109a cannot be executed simultaneously with it and they are taken one after the other after the end of the measurement 105a.

Not until all the measurements have been taken in the position of the patient couch is this position changed and the measurements of a part C of the measuring sequence start. Only the measurements 103c to 107c have to be taken in this position, it being possible for 103c and 105c to be executed in parallel again. The patient couch is then displaced again and a part B of the measuring sequences starts, which is equivalent in structure to part A and comprises the measurements 103b to 109b. Finally a part D of the measuring sequence is carried out taking into account measurements 103d and 105d in a fourth position of the patient couch. When using the predetermined measuring sequence the patient couch is only positioned four times, each time once for one of the four parts of the measuring protocol. If a measuring sequence according to the order of measurements in FIG. 3 were used, the patient couch would have to be displaced thirteen times.

A further advantage of the measuring sequence in FIG. 4 is the possibility of modifying subsequent measurements. This can be done for example by varying the measuring parameters, which influence subsequent measurements. It would therefore be possible during one of the measurements in part A of the measuring sequence to modify the PET measuring parameters of the subsequent measurements 103b to 103d without influencing the measurement 103a in the process. It is thus possible to be responsive in respect of ongoing optimization even during a measurement. Subsequent measurements then take place with the modified parameters.

To produce the measuring sequence the measuring protocols 103 to 109 are broken down into their individual measurements 103a to 109b (see also method step S5 in FIG. 2). Once the measurements that can be executed in parallel have been identified (method steps S11 to S19 in FIG. 2), the measurements 103a to 109b are rearranged and the measuring sequence is thus produced (method step S21 in FIG. 2). To this end the measurement 103a is moved to the start of the measuring sequence according to the measuring protocol 101, while the further measurements 103b to 103d of the measuring protocol 103 are moved to the end. The measurement 105a is taken in the same position as the measurement 103a and is therefore left after the measurement 103a in the measuring sequence. As they can be executed simultaneously, this is marked accordingly in the measuring sequence. The measurements 105b to 105d are in turn moved to the end of the measuring sequence. The same happens with the measurements 107a to 109b of the measuring protocols 107 and 109. Once all the measurements 103a to 109a of a region of the patient have been ordered accordingly, the measurements 103b to 109b are dealt with in a similar manner. This assigns the individual measurements 103a to 109b accordingly to their examination regions.

To improve or even optimize the regions, it is also possible to reorganize the parts of the measuring sequence in such a manner that part C takes place before part B, as in the example in FIG. 4.

Alternatively it is possible for the measurements 105 to 107 to be broken down and the possibility of parallel execution to be determined successively rather than jointly. Thus the measuring protocol 103 is broken down first and the measurements 103b to 103d moved to the end of the measuring sequence as described above. The measuring protocol 105 is then broken down into its measurements 105a to 105d, the regions with the measurements 103a to 103d are compared and the measurements 105b to 105d are moved to the end of the measuring sequence. The same happens successively with the measuring protocols 107 and 109, until all the measurements 103a to 109b have been ordered according to the regions to be examined. The possibility of parallel execution can be determined and marked for example jointly after the ordering of the measurements 103a to 109b or after the ordering of the respective region.

In the example embodiments described it is possible in each instance to modify measurements still to be executed, while another measurement in the measuring sequence is being taken. This saves time, as detailed planning does not have to be completed before measuring starts.

The described example embodiments for example comprise different selected measuring protocols. Instead of the measuring protocols specified here, any measuring methods can be deployed within the execution of the invention.

What is claimed is:

1. A method for planning a combined examination of an examination object using two imaging modalities, with measurements being taken in at least two regions of the examination object, comprising:

generating, by a processor associated with the two imaging modalities, a first plan including at least one first measuring protocol of a first imaging modality of the two imaging modalities, the first plan including at least one measurement in a first region of the at least two regions and at least one measurement in a second region of the at least two regions, each of the at least two regions having a respective couch position;

generating, by the processor, a second plan including at least one second measuring protocol of a second imaging modality of the two imaging modalities, the second plan including at least one measurement in the first region, wherein the second imaging modality is Positron Emission Tomography;

breaking the first and second planned measuring protocols into a plurality of individual measurements;

selecting a first of the plurality of individual measurements from the first planned measuring protocol;

selecting a second of the plurality of the individual measurements from the second planned measuring protocol;

comparing the selected first and second individual measurements;

determining whether the selected first and second individual measurements can be executed simultaneously;

determining whether all of the plurality of individual measurements from the first planned measuring protocol have been compared with all of plurality of individual measurements from the second planned measuring protocol; and generating a combined measuring sequence by arranging the measurements based on the comparison such that measurements in the same regions are taken simultaneously, and such that a time associated with executing the combined measuring sequence is less than a combined time associated with executing the first measuring protocol and the second measuring protocol individually.

2. The method as claimed in claim 1, wherein when arranging the measurements, measurements with identical examination regions are grouped together into groups, and the groups are arranged one after the other in the sequence.

3. The method as claimed in claim 2, wherein the measurements are arranged in such a manner that measurements that are executable in parallel by both modalities are executed at identical times in the measuring sequence.

4. The method as claimed in claim 1, wherein the measurements are arranged in such a manner that measurements that are executable in parallel by both modalities are executed at identical times in the measuring sequence.

5. The method as claimed in claim 1, wherein the generating of the combined measuring sequence comprises:
identifying measurements executable in parallel by the two modalities based on the comparison; and
simultaneously arranging the measurements, executable in parallel, in the measuring sequence.

6. The method as claimed in claim 5, wherein the identifying of measurements executable in parallel comprises:
determining relative position of the examination volumes of the two modalities, and
determining measurements of different modalities, in which the relative position of the regions to be examined is identical to the determined relative position of the examination volumes.

7. The method as claimed in claim 1, wherein the generating of the combined measuring sequence comprises:
moving a first measurement of the at least one measuring protocol of the first modality to a start of the measuring sequence;
arranging further measurements of the first measuring protocol at the end of the measuring sequence;
identifying measurements of the second modality, which have the same region to be examined as the first measurement of the first modality;
inserting the identified measurements after the first measurement;
arranging other measurements of the second measuring protocol at the end of the measuring sequence; and
repeating the moving, arranging, identifying, inserting and arranging with the further measurements after the identified measurements of the second modality, until all the measurements are ordered according to their regions to be examined.

8. The method as claimed in claim 1, wherein the modalities are present in a combined diagnosis apparatus and the regions of the examination object are brought into the examination volume by moving a patient couch and the combined measuring sequence is produced in such a manner that the number of movements of the patient couch during the measuring sequence is reduced.

9. The method as claimed in claim 8, wherein the measurements and the displacements of the patient couch are arranged temporally in the measuring sequence in such a manner that the patient couch is only displaced, when all the measurements to be taken in the previously assumed position of the patient couch are completed.

10. The method as claimed in claim 8, wherein the modalities have isocentric examination volumes.

11. The method as claimed in claim 8, wherein the measurements are simultaneously executable by the modalities.

12. The method as claimed in claim 8, further comprising determining a sequence for examining the regions.

13. The method as claimed in claim 8, wherein the number of movements of the patient couch during the measuring sequence is minimized.

14. The method as claimed in claim 1, wherein the measuring sequence is carried out so as to take as little time as possible.

15. The method as claimed in claim 1, wherein the modalities have isocentric examination volumes.

16. The method as claimed in claim 1, wherein the measurements are simultaneously executable by the modalities.

17. The method as claimed in claim 1, further comprising determining a sequence for examining the regions.

18. A method for carrying out a combined examination of an examination object using two imaging modalities, comprising:
planning the examination based upon the method as claimed in claim 1, with production of the measuring sequence taking place, while a first of the measurements is being taken and the measuring sequence being carried out after the first measurement is taken.

19. The method as claimed in claim 18, wherein the planning of the measurements still to be taken is modifiable, while the combined measuring sequence is being carried out.

20. The method as claimed in claim 19, wherein each individual measurement is repeatable, while the combined measuring sequence is being carried out.

* * * * *